(12) United States Patent
Skaria et al.

(10) Patent No.: US 8,735,464 B2
(45) Date of Patent: May 27, 2014

(54) RADICALLY CURABLE URETHANE DIMETHACRYLATES AND COMPOSITIONS THEREOF FOR TOUGHER DENTAL PROSTHETICS

(71) Applicant: Pulpdent Corporation, Watertown, MA (US)

(72) Inventors: Sunny Skaria, Concord, MA (US); Kenneth Berk, Newton, MA (US)

(73) Assignee: Pulpdent Corporation, Watertown, MA (US)

( * ) Notice: Subject to any disclaimer, the term of this patent is extended or adjusted under 35 U.S.C. 154(b) by 0 days.

(21) Appl. No.: 13/655,595

(22) Filed: Oct. 19, 2012

(65) Prior Publication Data

US 2013/0041067 A1    Feb. 14, 2013

Related U.S. Application Data

(62) Division of application No. 12/842,586, filed on Jul. 23, 2010, now Pat. No. 8,292,625.

(51) Int. Cl.
*A61F 2/00* (2006.01)

(52) U.S. Cl.
USPC ........... 523/115; 523/116; 523/113; 523/118; 525/123; 525/124; 525/125; 525/126

(58) Field of Classification Search
None
See application file for complete search history.

(56) References Cited

U.S. PATENT DOCUMENTS

| | | | |
|---|---|---|---|
| 4,457,818 A * | 7/1984 | Denyer et al. | 522/28 |
| 5,182,332 A | 1/1993 | Yamamoto et al. | |
| 5,376,691 A | 12/1994 | May et al. | |
| 5,486,570 A | 1/1996 | St. Clair | |
| 5,554,665 A | 9/1996 | Tateosian et al. | |
| 5,977,199 A | 11/1999 | Xie | |
| 6,023,547 A | 2/2000 | Tortorello | |
| 6,555,595 B1 | 4/2003 | Crivello et al. | |
| 6,709,271 B2 | 3/2004 | Yin et al. | |
| 6,747,097 B2 | 6/2004 | Chao et al. | |
| 6,943,202 B2 | 9/2005 | Zhu et al. | |
| 7,141,616 B2 | 11/2006 | Hecht et al. | |
| 7,279,505 B2 | 10/2007 | Phelan et al. | |

(Continued)

OTHER PUBLICATIONS

Fortin et al., "The Spectrum of Composites: New Techniques and Materials," J. Am. Dental Assoc., vol. 131, pp. 26S-30S, Jun. 2000.

(Continued)

*Primary Examiner* — James J Seidleck
*Assistant Examiner* — Peter A Salamon
(74) *Attorney, Agent, or Firm* — Sunstein Kann Murphy & Timbers LLP

(57) ABSTRACT

A radically curable polyurethane composite for dental restorations, including provisional restorations, includes polyurethane dimethacrylate prepolymers that have at least one flexible unit within a polyurethane dimethacrylate backbone, and one or more dimethacrylate monomers. Composite materials made with polyurethane dimethacrylate prepolymers of the invention exhibit superior and optimal properties of flexural strength and deflection-at-break relative to conventional dental resin composites. Composite materials of the invention also provide improved melt-resistance in response to the heat of grinding or finishing, thereby improving the fit of restorations made from the composite and preserving the finishing instruments. Methods of treating a tooth using the radically curable polyurethane composite and methods of making the polyurethane dimethacrylate prepolymers with flexible units is also provided. A kit including the radically curable polyurethane composite is also described.

11 Claims, 1 Drawing Sheet

(56) References Cited

U.S. PATENT DOCUMENTS

| | | |
|---|---|---|
| 7,371,782 B2 | 5/2008 | Stannard et al. |
| 7,402,271 B2 | 7/2008 | Morgan |
| 7,476,484 B2 | 1/2009 | Sailer et al. |
| 7,494,339 B2 | 2/2009 | Dias et al. |
| 7,604,552 B2 | 10/2009 | Melanson et al. |
| 8,292,625 B2 | 10/2012 | Skaria et al. |
| 2006/0111417 A1 | 5/2006 | Koilkonda et al. |
| 2006/0127325 A1* | 6/2006 | Bannister .................. 424/49 |
| 2007/0052796 A1 | 3/2007 | Choi et al. |
| 2008/0045643 A1 | 2/2008 | Henning et al. |
| 2010/0099058 A1 | 4/2010 | Wang |
| 2012/0129973 A1 | 5/2012 | Sun |

OTHER PUBLICATIONS

Christensen, "The Fastest and Best Provisional Restorations," J. Am. Dental Assoc., vol. 134, pp. 637-639, May 2003.

Hervás-Garcia et al., "Composite resins. A review of the materials and clinical indications," Med. Oral Patol Oral Cir. Bucal, vol. 11, pp. E215-E220, 2006.

* cited by examiner

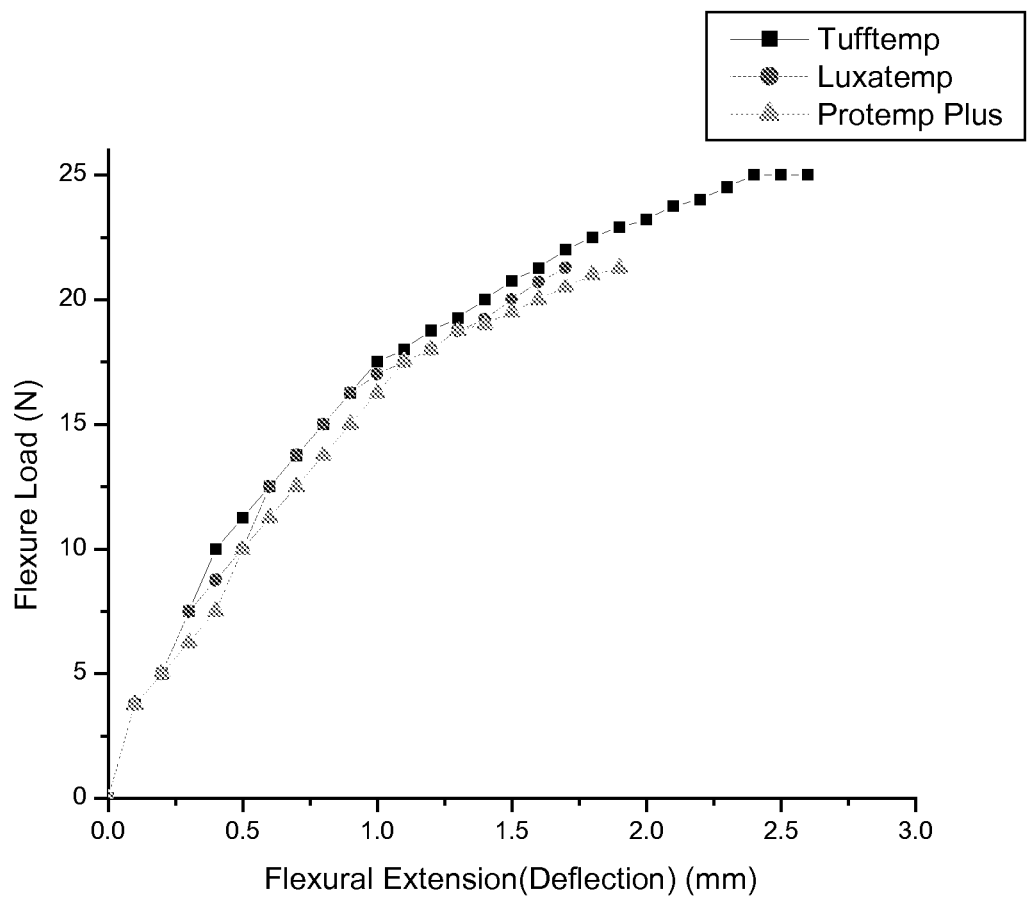

RADICALLY CURABLE URETHANE DIMETHACRYLATES AND COMPOSITIONS THEREOF FOR TOUGHER DENTAL PROSTHETICS

CROSS-REFERENCE TO RELATED APPLICATIONS

The present application is a divisional of U.S. patent application Ser. No. 12/842,586 filed Jul. 23, 2010, the disclosure of which is incorporated by reference herein in its entirety.

TECHNICAL FIELD

The present invention relates to radically curable polyurethane dimethacrylate prepolymers having flexible units and the synthesis and use thereof for the preparation of dental restorative materials.

BACKGROUND ART

Composite-based resins have made significant contributions to restorative dentistry. Improvements in such resins have facilitated an increase in prosthodontic therapy and aesthetic dentistry. One of the principal uses of composite resins is in the manufacture and application of provisional restorations. Provisional restorations are temporary prostheses that are placed on, or in place of, one or more teeth for a limited period, from several days to several months, and in some cases even longer, and which are designed to protect the tooth or teeth, provide masticatory function, maintain proper alignment of adjacent and opposing teeth, and remain in position until a permanent restoration is facilitated. As can be readily understood, the resin that comprises a provisional restoration must have the durability, toughness and physical properties to withstand mastication of hard food while maintaining a tight fit to the underlying tooth or teeth. It must also have an aesthetic appearance that matches or improves upon the appearance of the original teeth.

Dental resins typically contain three primary ingredients: (1) an organic binder or matrix of monomers; (2) inorganic filler; and (3) a coupling agent, often incorporated into a polymerization system. The qualities of the individual components that comprise a resin, particularly the monomers used, as well as synergistic properties derived from particular combinations of components, have an enormous impact on the aesthetic quality, durability and clinical utility of the resin. The most desirable resins possess high impact strength, high elasticity, high hardness, and dimensional stability with little tendency to swell through water absorption (which lowers strength).

The organic binder of composite resins is made up of a system of mono-, di- or tri-functional monomers. The monomer system can be viewed as the backbone of the composite resin system. Suitable monomers include ethylenically unsaturated compounds such as acrylic acid and methacrylic acid esters.

Filler particles vary from one composite-based resin to another, and each type of filler has its own distinctive characteristic. The filler portion of a composite-based resin has a significant effect on the qualities of the cured composite. For example, the size of a given filler particle can affect roughness and strength. As a general rule, the higher the loading of filler, the higher the strength of the final composite-based resin.

A polymerization system is often comprised of several components. These include polymerization initiators specific for a given type of polymerization system. For example, in chemically-activated systems, benzoyl peroxide and tertiary amines serve as a source of free radicals, which create propagating sites of polymerizing reactivity in carbon-carbon double bonds of the monomers. For light-activated resin composites, a diketone photoactivator is typically used.

Polymerization systems may also contain coupling agents to bond the filler particles to the organic resin matrix via silanating agents. This serves to improve the resin's physical properties by preventing hydrolytic breakdown along the filler/matrix interface. Hydrolytic breakdown of the filler/matrix interface can crack the resin through stress transfer.

Acrylic dental resins have been in use for over fifty years and continue to be used for the fabrication of provisional restorations. These materials are typically polymethylmethacrylate (PMMA) and methyl methacrylate (MMA). With acrylic resin, the fabrication of the provisional restoration usually requires mixing a powder and liquid together to form a paste that is placed in either a premade shell (tooth form), or into a template or carrier that is placed over the tooth preparation. These materials have adequate strength, are tooth-colored and have relatively good color stability over a few weeks. They can be smoothed and polished, are easily repaired, and are relatively inexpensive. PMMA resins have a sufficiently high glass transition temperature ($T_g$) to allow trimming, grinding and finishing of the cured material without causing the material to soften or distort. $T_g$ is the temperature at which a polymer goes from a hard, glass-like state to a rubber state. Since PMMA resins have a sufficiently high $T_g$, the heat of the grinding and finishing wheel used to trim, shape and finish the margins of the provisional restoration does not distort the resin. The material grinds and powders providing crisp and accurate margins. The accurate margins provide a good adaptation to the tooth preparation and gingival tissue.

However, repeated mixing of powder and liquid exposes the dentist and/or dental assistant to monomers that may be cytotoxic to users under certain conditions. Allergies to PMMA monomers are well documented, and these allergic reactions can be quite severe. PMMA products also have strong and objectionable odors. Furthermore, precise dispensing of PMMA products is difficult and mixing ratios generally vary according to user experience and desires. Because of these variations in proportions and mixing skills, physical properties can vary, irritation to oral mucosa can be exacerbated and there can be an increase in the exothermic reaction, heat gain, which can produce negative effects on the dental pulp if not mitigated with specific, seldom used additional techniques and materials.

In addition, PMMA materials are well known for shrinkage during polymerization leading to poorly fitting restorations. Following the initial insertion of the carrier matrix (template) filled with PMMA, the carrier matrix with partially polymerized PMMA restoration is removed from the mouth before the final set, and complete polymerization and hardening continues outside the mouth. The torque and manipulation applied when removing the carrier matrix can distort the provisional restoration, adding another contributing factor to the poor fit of PMMA provisional restorations.

Additional shrinkage continues to occur over time in the mouth due to the constant exposure to moisture in the oral environment. The changing dimensions of the PMMA restoration change the way the prostheses fit, causing them to come loose, and a PMMA restoration may need to be relined in cases deemed long term. The effect of shrinkage at the margins increases the micro-leakage of bacteria and may allow re-infection of the tooth prior to the placement of the final restoration.

Due to the deficiencies of the aforementioned PMMA acrylic resins, Bis-acrylic resins have become a popular material for provisional restorations. Bis-acrylic composites have less exotherm, are easier to mix precisely due to automix dispensing systems, are more polishable, more color stable, have better physical properties and shrink less than PMMA resins.

However, Bis-acrylics have a number of prominent disadvantages, including high cost, low Tg, difficulty in making repairs, brittleness, frequent breaking at pontic areas, suitability for single-unit provisionals only, and frequent debondings requiring re-cementation. Unique to bis-acrylic resins is a low glass transition temperature resulting in gumming up of finishing instruments and the routine softening and loss of margins at the tooth preparation interface. Bis-acrylics soften from the heat produced by the grinding and finishing instruments, and this distorts the margins. The bis-acrylic must then be relined and the margins must be re-established with flowable composites. This aspect is time consuming and may create resin compatability issues. Marginal integrity is critical to proper fit and the health of the gingival tissue.

Bis-acrylics have adequate flexural and compressive strengths, but are quite brittle, lacking the desired toughness and deflection at break. Also, they do not have a sufficient "memory effect" (also referred to as "temporary flexibility effect") to maintain an optimal marginal fit.

Increasing toughness and flexibility without sacrificing other properties is a great advantage in dental restorative applications. Various approaches have been tried to address these issues. In 1994, May et al. (U.S. Pat. No. 5,376,691) disclosed adding non-polymerizable additives (such as polyethylene glycol) or plasticizers (such as esters of phthalates), but these approaches yield polymers with inferior mechanical properties such as brittleness, incomplete curing, phase separation and leaching of non-polymerized additives. Recently, Orlowski et al. disclosed the use of polybutene in acrylate resins to increase the flexibility and decrease the brittleness of dental prosthetic materials. However, polybutenes are non-polymerizable, low Tg materials and may create micro-non-homogenieties in the resin; polybutenes may leach out of the cured resin matrix, decreasing the durability of the dental composite; and the addition of polybutenes will not eliminate the gumming of the crowns and bridge material on polishing.

Urethane dimethacrylate resins have been used to fabricate dental prostheses. Urethane dimethacrylate resins have excellent flexural characteristics but lack flexibility. Also, high amounts of low molecular weight diurethane dimethacrylate in the resin formulation increases the exothermic heat and increases polymerization shrinkage due to the high concentration of double bonds.

SUMMARY OF EMBODIMENTS

Embodiments of the present invention provide a radically curable urethane dimethacrylate composite for dental restorations that provides superior and synergistic properties of hardness, toughness and flexural strength while maintaining the aesthetics required of dental materials.

In one embodiment of the invention, a radically curable polyurethane composite for dental restoration is provided. The composite includes (A) about 5-45% by total weight of the composite of a polyurethane dimethacrylate prepolymer blended in at least one aprotic methacrylate monomer, wherein the prepolymer includes at least one flexible unit within a polyurethane dimethacrylate backbone, and (B) about 15-60% by total weight of the composite of one or more dimethacrylate monomers. In particular embodiments, the flexible unit incorporated or inserted into the backbone of the prepolymers may be hydrogenated polybutadiene diol, polyester diol, polyether diol and combinations thereof. In more particular embodiments, the composite includes a urethane dimethacrylate that has at least one polybutadiene molecule within the urethane dimethacrylate. In various embodiments, the one or more dimethacrylate monomers may be polyether dimethacrylate, alkyl dimethacrylate, polyester dimethacrylate and combinations thereof.

The aprotic methacrylate monomers may be triethylene glycol dimethacrylate, tetraethylene glycol dimethacrylate, polyethylene glycol dimethacrylate, polyethylene glycol methacrylate monomethyl ether, tetramethylene dimethacrylate, hexamethylene dimethacrylate, octamethylene dimethacrylate, and/or dodecamethylene dimethacrylate.

The radically curable polyurethane composite may also include a photoinitiator system. The photoinitiator system may further include a polymerization inhibitor such as butylated hydroxytoluene or hydroquinone monomethyl ether, and combinations thereof. In certain embodiments, the photoinitiator system may comprise a light sensitive photoinitiator selected from a group comprising camphorquinone, benzil, acylphosphine oxide, and an amine co-initiator. The radically curable polyurethane composite of certain embodiments may further include a nonreactive filler. This filler may be, for example, barium glass, barium borosilicate glass, strontium glass, quartz, submicron silica and combinations thereof.

The radically curable polyurethane composite of certain embodiments may further include a polymerization catalyst. The polymerization catalyst may be selected from a group comprising dibenzoyl peroxide, 2,2-(4-methylphenylimino) diethanol, dimethylaminoethyl methacrylate, N,N-dimethyl-p-toluindine, N,N-dimethylaminoethyl-methacrylate, benzoinmethylether and combinations thereof.

The radically curable polyurethane composites of embodiments of the invention are characterized by a number of superior properties that facilitate use in dental applications. For example, certain embodiments may be characterized by a deflection-at-break of 2.3 to 3.2 mm after curing.

Embodiments of the invention may also include methods of treating a tooth. The methods generally include providing a radically curable polyurethane composite for dental restoration, which includes (A) about 5-45% by total weight of the composite of a polyurethane dimethacrylate prepolymer blended in at least one aprotic methacrylate monomer and the prepolymer includes at least one flexible unit within a polyurethane dimethacrylate backbone, and (B) about 15-60% by total weight of the composite of one or more dimethacrylate monomers. The method further includes applying the composite material to at least a portion of a surface of one or more teeth and curing the polymerizable composite material so that the composite material polymerizes.

Particular embodiments of the methods disclosed herein further include the addition of one or more dimethacrylate monomers, a catalyst, and non-reactive filler to the composite. Furthermore, the flexible unit of the prepolymers may be polybutadiene diol, polyester diol and/or polyether diol.

Additional embodiments of the methods may involve trimming the polymerized composite so that it substantially replicates the surface of one or more teeth and creates an anatomically correct margin. Optionally, a sealant may be applied to the polymerized composite. In a particular embodiment, the polymerized composite includes a provisional dental prosthesis.

Embodiments of the invention utilize a radically curable polyurethane dimethacrylate prepolymer for use in dental compositions. The prepolymers include at least one reactive diol inserted within a polyurethane dimethacrylate backbone. In certain embodiments, the reactive diol may be hydrogenated polybutadiene diol, polyester diol and/or polyether diol. In more particular embodiments, the reactive diol may be hydrogenated polybutadiene.

The radically curable polyurethane dimethacrylate prepolymers of embodiments of the invention may be made or produced by reacting at least one diisocyanate monomer with a reactive diol in the presence of a catalyst to form a diisocyanate-diol prepolymer and blending the diisocyanate prepolymer in at least one aprotic methyacrylate monomer. In certain embodiments, the diisocyanate monomer may be dicyclohexyl methane diisocyanate, tetramethyl xylene diisocyanate, isophorone diisocyanate, hexamethylene diisocyanate, 4,4 diphenylmethane diisocyanate, and/or tolulene diisocyanate. The aprotic methacrylate monomer may be triethylene glycol dimethacrylate, tetraethylene glycol dimethacrylate, polyethylene glycol dimethacrylate, polyethylene glycol methacrylate monomethyl ether, tetramethylene dimethacrylate, hexamethylene dimethacrylate, octamethylene dimethacrylate, and/or dodecamethylene dimethacrylate. In certain embodiments, the reactive diol may be hydrogenated polybutadiene diol, polyester diol and/or polyether diol.

In particular embodiments, the diisocyanate prepolymer may be further reacted with an ethylenically unsaturated monohydroxy compound. The ethylenically unsaturated monohydroxy compounds may be hydroxylpropyl methacrylate, hydroxylethylmethacrylate, hydroxyethyl acrylate, hydroxypropyl acrylate, monohydroxy caprolactone methacrylate, hydroxyl butyl methacrylate, and/or monohydroxy polyethylene glycol methacrylate. In a yet more particular embodiment, the diisocyanate-diol prepolymer may be formed by reacting isophorone diisocyante and saturated hydroxyl-terminated polybutadiene in the presence of hexamethylene dimethacrylate and dibutyltin dilaurate to form a polyisocyanate prepolymer in 20% hexamethylene dimethacrylate. Additionally, 2-hydroxyethylmethacrylate may be added in the presence of a phenolic inhibitor, and the reaction may be monitored with Fourier transform infrared spectroscopy until no free isocyanate groups are detected. In other embodiments, a phenolic polymerization inhibitor may be added to the radically curable polyurethane dimethacrylate prepolymer.

Further embodiments of the invention comprise a dental restoration kit of a radically curable polyurethane composite, wherein the composite includes diisocyanate-polybutadine prepolymers and a provisional sealant.

BRIEF DESCRIPTION OF THE DRAWINGS

The foregoing features of embodiments will be more readily understood by reference to the following detailed description, taken with reference to the accompanying drawing, in which:

FIG. 1 is a graph showing flexural load versus flexural extension (deflection) for various materials compared to embodiments of the present invention.

DETAILED DESCRIPTION OF SPECIFIC EMBODIMENTS

Polyurethane dimethacrylates are produced by the polyaddition reaction of a polyisocyanate with a polyalcohol or diol in the presence of a catalyst and other additives and then end-capping with a monohydroxy methacrylate. In the present disclosure, a prepolymer is obtained by the addition reaction of a diisocyanate and a diol end-capped with a monohydroxy methacrylate. The reaction product is a polymer containing the urethane linkage, —RNHCOOR'—.

Polyurethanes with various flexible units may be synthesized and used in the preparation of flexible coatings, elastomers, and other applications where toughness and flexibility are required. Polyurethanes with flexible polyester soft segments lack hydrolytic stability and polyurethanes with polyether segments (e.g., U.S. Pat. No. 7,494,339) tend to absorb water and lose dimensional stability.

Polybutadienes may be used for the preparation of toughened polyurethanes. Uses include the preparation of golf balls (U.S. Pat. No. 7,604,552) and flexible coatings (U.S. Pat. No. 6,747,097 and US application no. 20070052796). An example is a commercially available polybutadiene methacrylate, CN301 from Sartomer. However, this material has been found to be aesthetically inferior and to be incompatible with monomers used in these formulations.

Embodiments of the present invention relate to polymerizable polyurethane composite resins and methods of making and using such materials in dental prosthetics. Embodiments of the present invention provide a polymerizable polyurethane dimethyacrylate composite material for dental applications with improved strength, elasticity, hardness and aesthetics. Surprisingly, it has been found that these qualities can be obtained with the incorporation of suitable flexible units, such as hydrogenated polybutadiene, polyolefins, polyesters and polyethers, within the backbone of a polyurethane dimethacrylate prepolymer. The composite material comprises a formulation of monomers and novel prepolymers that yield dental prostheses or crowns with resistance to discoloration, and surprising and superior toughness and deflection-at-break characteristics relative to conventional dental resins.

Another notable feature of the radically curable polyurethane composite of embodiments of the invention is its response to heat generated by finishing or grinding. Upon such finishing or grinding, it transitions to a powder rather than a soft, gum-like state. The "gumming" of a temporary crown during trimming or polishing can result in a poor fitting or loose crown, and may require a second patient visit to repair or fix the crown. Embodiments of the present invention, therefore, exhibit improved prosthetic fit and do not create a "gumming up" of the finishing instruments. Without being limited to a particular principal of operation, it is believed that this effect is created by a relatively high Tg of the polymerized composite.

The embodiments disclosed herein utilize a urethane dimethacrylate prepolymer prepared from hydrolytically and color-stable flexible units. Polyurethane dimethacrylate prepolymers for use in embodiments of the invention may be prepared by the addition reaction of an aliphatic diisocyanate and an odorless, clear saturated liquid polyol, which is end-capped with a hydroxyl methacrylate monomer. The use of saturated polyols as flexible units incorporated within a polyurethane dimethacrylate backbone provides light-stability and wear resistance, and enables a formulation with superior mechanical properties and resistance to heat and discoloration. Flexible units for use in embodiments of the present invention include, for example, hydrogenated polybutadiene diol, hydrogenated polyester diol, polyether diol, and/or polyolefins.

The flexible units, therefore, comprise polyurethane dimethacrylate prepolymers for use in a radically curable polyurethane composite for dental restorative composition, including provisional restorations. In particular embodiments, the radically curable composite comprises polyurethane dimethacrylate with flexible units, urethane dimethacrylate, alkyl dimethacrylates, glass fillers, free radical catalysts, activators and photoinitiators. The composite may be self-cured (also referred to as mix cure or chemical cure), heat cured, light cured (UV or other radiation) or may comprise a dual-cure system (a combination of self-cured and light-cured materials).

The amount of polyurethane dimethacrylate prepolymers with flexible units may vary from about 5-45% by total weight of the final composite material. Embodiments of the polyurethane composite also include one more dimethacrylate monomers, which may vary from about 15-60% by total weight of the final composition. Suitable dimethacrylate monomers include urethane dimethacrylate, polyether dimethacrylate, alkyl dimethacrylate, polyester dimethacrylate and combinations thereof. The amount of dimethacrylate monomers may be adjusted to control the strength of the material through co-polymerization, enhanced polymerization with additional co-monomers, and impart some further hydrophilic or hydrophobic characteristics to the material. 2-hydroxyethyl methacrylate is an example of such a hydrophilic co-monomer. 1,6 hexamethylene dimethacrylate is an example of a hydrophobic co-monomer.

The polymerizable polyurethane composite material includes polyurethane dimethacrylate prepolymers with at least one flexible unit, one or more dimethacrylate monomers, and may further include a nonreactive filler, a polymerization system, additional co-monomers, and water. The composite material may additionally contain other adjuncts to impart convenient handling characteristics and satisfy setting or curing requirements and other suitable qualities useful in restorative dentistry. Depending on the chemical configuration of the dimethacrylate monomers or other co-monomers, significant differences in polymerization kinetics and mechanical properties of the formed dental resins, such as final double bond conversion, modulus, flexural strength and hardness, volume shrinkage, and biocompatibility, can be achieved. Co-monomers for embodiments of the invention include, but are not limited to, polymerizable compounds such as diurethane dimethacrylate; hydroxyethylmethacrylate; trimethyol propane trimethacrylate; 1,6 hexamethyene dimethacrylate; polyethylene glycol dimethacrylate; and bis glycidyl dimethacrylate (BIS-GMA).

Non-reactive fillers suitable for embodiments of this invention are ones that will not react with the organic matrix. Nonreactive fillers used in embodiments of the invention include barium glass, barium borosilicate glass, strontium glass, quartz, submicron silica and combinations thereof, and other materials well known to those skilled in the art. The filler is made up of particles used to impart strength to the composite structure. The filler may contain particles of varying sizes. For example, the filler may include micron-sized or submicron-sized particles of silica ($SiO_2$). Micron-sized particles typically provide density, while submicron-sized particles typically act as a thickening and suspending agent. Further, the particles may be silanated, i.e., have a coating of silane. The amount of filler varies from about 1% to 80% by weight, depending on whether the material is used as a glaze suitable for sealing a margin of a restoration or for sealing a pre-carious lesion, or as a highly filled, restorative material suitable for high strength, low wear applications such as Class I or Class II restorations. An intermediate filled material, in the range of about 25-50% by weight, would be suitable for placement as a pit and fissure sealant, and as a Class I, Class III, Class IV or Class V restorative material.

The polymerization system can be activated by heat (heat cured), chemicals (self-cured, mix cured), light or combinations thereof (dual-cure). Light-activated (or photocurable) resins depend on free radical initiation by an alpha diketone (e.g., camphoroquinone) in combination with a tertiary aliphatic amine reducing agent (e.g., 4-n,n-dimethylamino-phenyl-ethanol, or dimethylamino ethyl methacrylate). Chemically-curable resins use an initiator of benzoyl peroxide or other organic peroxide in combination with an aromatic tertiary amine (n,n-dihydroxyethyl-p-toluidine).

In certain embodiments of the invention, light curing compounds or photoinitiators include such compounds as camphorquinone, acylphosphine oxide (Lucerin TPO®), benzil, methyl benzil ether, and phenyl-propanedione. Other photoinitiators that may be used are known to those skilled in the art.

The polymerization system may also contain an accelerator (e.g, dimethylaminoethyl methacrylate, ethyl-4 dimethylaminobenzoate, or N,N-cyanoethyl-methylaniline), which acts on the initiator and allows curing to take place in a clinically acceptable time. Other accelerators that may be used are known to those skilled in the art.

Two-part chemical cure formulas of embodiments of this invention may require separation of polymerization accelerators from the initiator. Such an initiator may include benzoyl peroxide, cumene hydroperoxide, lauryl peroxide or any of a number of widely recognized organic peroxides for free radical or cationic/anionic polymerization reactions.

Composite resins of embodiments of the invention may also contain a stabilizer or inhibitor system such as hydroquinone monomethyl ether to extend the product's storage life by restricting spontaneous polymerization, decreasing sensitivity to ambient light and prolonging working time before the resin sets. The polymerization system may also contain absorbers of ultraviolet light at wavelengths below 350 nm, such as 2-hydroxy-4-methoxybenzophenone, to provide color stability and eliminate the effects of UV light on the amine compounds in the initiator system, which can cause discoloration.

To facilitate manufacturing and clinical handling, embodiments of the invention may be diluted with other low-viscosity (i.e., low molecular weight) monomers, which are considered viscosity controllers. Examples include bisphenol A dimethacrylate (Bis-DMA), ethylene glycol dimethacrylate (EGDMA), triethylene glycol dimethacrylate (TEGDMA), methyl methacrylate (MMA) and/or urethane dimethacrylate (UDMA).

In particular embodiments of the invention, flexibility and strength is imparted to the composite resin through a radically curable diurethane prepolymer that includes at least one reactive diol inserted within a polyurethane dimethacrylate backbone. The incorporation of the reactive diol or other long alkyl or alkene units enhances flexibility. In this capacity, the reactive diol functions as a flexible unit.

In certain embodiments, the reactive diol is selected from a group comprising hydrogenated polybutadiene diol, polyolefin diol, hydrogenated polyester diol and polyether diol. In yet more particular embodiments, the incorporation of suitable long flexible units is accomplished by inserting at least one hydrogenated or saturated polybutadiene diol within a diurethane dimethacrylate backbone, such that a diisocyanate-diol prepolymer is formed, which may be represented by the formula:

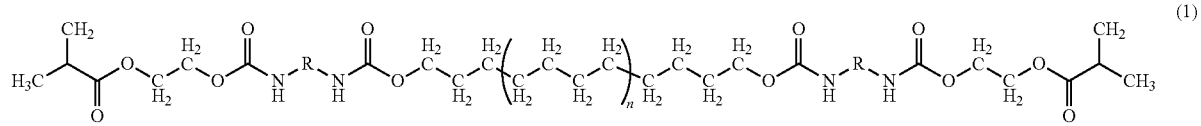

(1)

wherein R is an organic chain.

The incorporation of flexible units within a urethane dimethacrylate backbone as utilized in embodiments of the invention achieves unexpected and surprising results in flexural strength and toughness (as determined by deflection-at-break properties). Whereas ordinary composite resins are limited by a tradeoff between flexural strength and toughness, embodiments of the present invention achieve synergistic levels of both properties.

In addition to these superior material properties, embodiments of the invention possess the aesthetic properties required for dental applications. Principally, the composite resins disclosed herein are surprisingly resistant to discoloration. Particular embodiments of the invention incorporate hydrogenated (or saturated) flexible units, thereby eliminating many of the functional double bonds that may be a source of discoloration upon oxidation or UV irradiation.

In one particular embodiment of the invention, a polyurethane dimethacrylate with flexible units is prepared by charging 590 parts of a commercially available hydrogenated polybutadiene polyol (e.g., Krasol® Hydrogenated Hydroxyl-Terminated Polyolefin), 200 parts of hexamethylene dimethacrylate monomer and 130.7 parts of isophorone diisocyante in a steel reaction vessel equipped with mechanical stirrer and thermometer. The hydroxyl:isocyanate ratio of the rubber diol to diisocyanate is optimal at approximately 1:2. A catalyst such as dibutyl tin diluarate (150 ppm) is added. The reaction is continued at 70-80° C. for approximately 3 hours. The temperature is then lowered to 40-50° C. and 82 parts of 2-hydroxyethyl methacrylate monomer containing 2400 ppm monohydroxy hydroquinone (MEHQ) inhibitor added. The temperature of the reaction is then increased again to 70-80° C. This reaction results in diisocyanate-diol prepolymers of a urethane dimethacrylate backbone with polybutadiene incorporated therein, or "rubberized" urethane dimethacrylate, blended in 20% hexamethylene dimethacrylate. The prepolymers may have a Brookfield viscosity of approximately 30,000 cP and an inhibitor concentration of 200 ppm.

In other embodiments, the prepolymers comprise a flexible polyester or polyolefin unit within a diurethane dimethacrylate backbone. These embodiments, and the components used in their synthesis, may be represented by the following formulas, wherein $R_1$ and $R_2$ are any alkyl chain and $R_3$ is a urethane unit with a polyester or polyolefin chain.

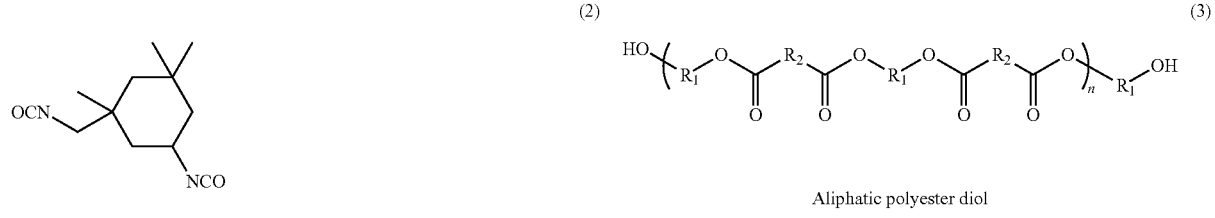

(2)

IPDI (3)

Aliphatic polyester diol (4)

KRASOL HLBH P2000

(5)

DIURETHANE DIMETHACRYLATE chain:

(6)

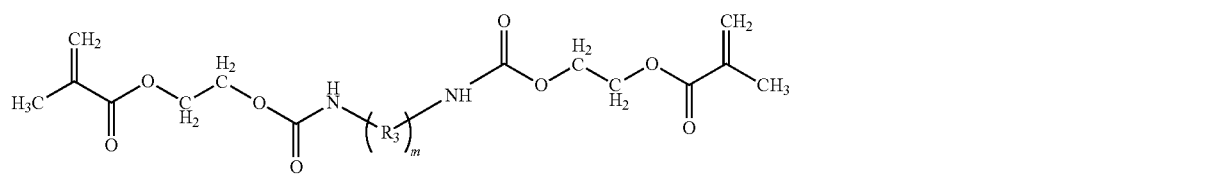

$R_3$ = Urethane units with polyolefin or polyester chains

A polyurethane dimethacrylate with polyester flexible units may be prepared by charging 526 parts of a polyester diol with a molecular weight of approximately 1000 (e.g., Oxyester® T1136 from Degussa), 130 parts of polyethylene glycol dimethacrylate monomer, and 208 parts of isophorone diisocyante in a steel reaction vessel equipped with mechanical a stirrer and thermometer. The hydroxyl:isocyanate ratio of the diol to diisocyanate is optimal at approximately 1:2. A catalyst such as dibutyl tin diluarate (150 ppm) is added. The reaction is continued at 70-80° C. for approximately 3 hours. The temperature is lowered to 40-50° C., and 132 parts of 2-hydroxyethyl methacrylate monomer containing 2400 ppm monohydroxy hydroquinone (MEHQ) inhibitor is added. The temperature of the reaction is then further increased to 70-80° C. The result of this reaction is polyurethane dimethacrylate prepolymers with polyester flexible units incorporated therein, blended in 14% polyethylene glycol dimethacrylate. The product may have a Brookfield viscosity of 45,000 cP and an inhibitor concentration of 200 ppm.

Diisocyanate monomers for use in the examples above and in other embodiments of the invention include dicyclohexyl methane diisocyanate, tetramethyl xylene diisocyanate, isophorone diisocyanate, hexamethylene diisocyanate, 4,4 diphenylmethane diisocyanate, and tolulene diisocyanate.

The prepolymers are blended in at least one aprotic methacrylate monomer. These monomers may be selected from a group comprising triethylene glycol dimethacrylate, tetraethylene glycol dimethacrylate, polyethylene glycol dimethacrylate, polyethylene glycol methacrylate monomethyl ether, tetramethylene dimethacrylate, hexamethylene dimethacrylate, octmethylene dimethacrylate, and dodecamethylene dimethacrylate.

In alternative embodiments, the diisocyanate prepolymer may be reacted with an ethylenically unsaturated monohydroxy compound selected from a group comprising hydroxyl propyl methacrylate, hydroxylethylmethacrylate, hydroxyethyl acrylate, hydroxypropyl acrylate, monohydroxy caprolactone methacrylate, hydroxyl butyl methacrylate, and monohydroxy polyethylene glycol methacrylate.

It should be readily understood that in addition to the polybutadiene and polyester diols discussed above, other reactive diols may used to generate the prepolymers of embodiments of the invention. Other reactive diols include polyether and polyolefin.

Both the superior material and aesthetic properties (as well as other hygienic properties) of certain embodiments of the invention may be enhanced by ensuring that the polyurethane dimethacrylate prepolymers with flexible units are made under reaction conditions that are continued until no free isocyanate groups remain. An absence of free isocyanate indicated the conversion of monomers to prepolymers. In other words, it is a reflection of reacted versus unreacted material. Reducing the content of unreacted diisocyanate in the reaction by ensuring complete polymerization of the prepolymers reduces toxicity and improves mechanical performance. The absence of free isocyanate may be confirmed by Fourier transform infrared spectroscopy (FTIR) or other suitable means known to those of skill in the art. For example, the reactions above may be continued until the FTIR shows no peak corresponding to the free isocyanate group ($2270 cm^{-1}$). The absence of free isocyanate may be further confirmed by titration.

A method of using the composite material includes providing the composite material, applying it to one or more teeth, and then curing by activating the polymerization system such as by applying light to activate a light curing compound. For dual cure formulations, the materials are mixed together prior to application to the tooth.

When the composite material is used for treating a tooth, it may be trimmed so that it substantially replicates the surface of one or more teeth and creates an anatomically correct margin. In particular embodiments, the anatomically correct margin may be such that the tooth-to-restoration contact is not visible to the naked eye. A sealant may optionally be applied to the polymerized composite.

The polymerized composite may comprise a provisional dental prostheses. In alternative embodiments, the polymerized composite may comprise part of a permanent or semi-permanent dental prosthetic such as a crown or bridge, a denture or partial denture, or an orthodontic appliance.

The composite material may be applied as a two-part polymerization system with an accelerator side and a catalyst side. The accelerator side may comprise the polyurethane dimethacrylate prepolymers with flexible units end-capped with a hydroxyl methacrylate monomer. The accelerator side may further comprise one or more dimethacrylate comonomers, one or more non-reactive fillers, a photoinitiator system, amine and butylated hydroxy toluene to protect the polymers from oxidative degradation. The catalyst side may comprise one or more dimethacrylate comonomers, one or more non-reactive fillers, a polymerization catalyst (e.g., benzoyl peroxide) and butylated hydroxy toluene. Other components as known to those skilled in the art may be included in either side of the reaction to modify the polymerization reaction and the properties of the polymerized composite.

The two-part system may comprise the acceleration side and the catalyst side in separate chambers of syringe-type dispensers. Other suitable dispensers may be used as known to those of skill in the art. The syringes may be packaged as part of a kit for dental restorations. The kit may also contain a sealant, glaze, add-on or other components to enhance the aesthetics of a provisional restoration made with the kit.

To further illustrate the attributes of embodiments of the present invention and the qualities imparted to the composite materials by the polyurethane dimethacrylate prepolymers, the following examples are provided. However, embodiments of the present invention are not to be construed as being limited thereto. Unless otherwise indicated, all percentages are by weight.

In the following examples, the polyurethane dimethacrylate prepolymers with flexible units are prepared using either hydrogenated polybutadiene diol (examples 4, 6-7) or polyester (example 5) as the "flexible" polyol.

Test Methods

Flexural strength and deflection at break were determined by using a three point bending test as specified by ISO specifications 4049. The flexural test specimens were fabricated according to a group 4049 specification (25 mm length×2 mm width×2 mm thickness) using a polypropylene mold (n=5 per materials, storage conditions, formulations). The material was injected into the mold, and after injection the mold was covered with a transparent Mylar film and a glass plate tightly placed over the mold. The mold was then placed in an incubator at 37° C. for 10 min. Excess material was removed by wet grinding on 600 grit silicon carbide paper directly before testing and the specimen's width and thickness were measured using a digital micrometer. The Flexural strength and deflection at break were measured on an Instron Model 1011 Universal testing machine used at crosshead speed of 1 mm/min to record the stress-strain curve and determine the deflection and force at break. The flexural strength was calculated using $FS=3FL/2bt^2$, where F is the Force (N) at break, L=span length (mm), b is the width (mm) and t is the thickness (mm).

The toughness of the materials was determined by measuring the area under the stress-strain curve obtained from the flexural strength measurements.

For compressive strength measurements (n=5), specimens were fabricated by injecting material into a polypropylene cylindrical molds of 4 mm diameter and 6 mm length. The material was allowed to cure at 37° C. for 10 min. The diameter and length of the specimens were measured using a micrometer. The compressive strengths of the specimens were measured on a Instron Universal analyzer with a crosshead speed of 10 mm/min. The force at break is then calculated as CS=Force at break(N)/Area of cross-section.

One of the major problems associated with resin-matrix composite (in particular crown and bridge material) that leads to failure of restorations is fracture within the body of restorations. This is related to many factors such as flexural strength, fracture toughness, marginal disintegration under stress, quality of fit, and toughness of the materials. These properties are usually evaluated by testing flexural strength, flexural modulus, and toughness of the materials.

Temporary crown and bridge materials should have optimum characteristics and toughness or deflection at break. The initial (within 10 min. of fabrication) flexural strength and flexural modulus of the material is of a great concern as this is the period at which plastic deformation of the prostheses, while removing the material from the fabrication site takes place. This deformation can cause loose fitting crowns and bridges. The 10 min. and 24 h flexural properties of provisional crown and bridge materials are presented in Table 1.

EXAMPLE 1

Accelerator Side:

| Ingredient | Percent |
| --- | --- |
| Urethane dimethacrylate | 27.0 |
| Polyurethane dimethacrylate with Flexible Units | 0.0 |
| polyether dimethacrylate | 7.5 |
| alkyl dimethacrylate | 26.5 |
| Glass filler | 33.0 |
| amorphous silica | 5.2 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.

Properties:
Flexural strength (Mpa): 71.2
Deflection-at-break (mm): 1.8
Compressive strength (Mpa): 300
Results:
Example 1 demonstrates a polymerized composite material without inclusion of polyurethane dimethacrylate prepolymers with flexible units. Although this example has excellent flexural and compressive strength, it is extremely brittle, as reflected in its low deflection-at-break value. This brittleness results in poor fit when used to make a dental prosthetic and lessens the durability of the composite.

EXAMPLE 2

Accelerator Side:

| Ingredient | Percent |
| --- | --- |
| Urethane dimethacrylate | 27.0 |
| Polyurethane dimethacrylate with Flexible Units | 0.0 |
| polyether dimethacrylate | 26.5 |
| alkyl dimethacrylate | 7.5 |
| Glass filler | 33.0 |
| amorphous silica | 5.2 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.

Properties:
Flexural strength (Mpa): 43.3
Deflection-at-break (mm): 3.4
Compressive strength (Mpa): 226
Results:
Example 2 demonstrates another polymerized composite material formulation without inclusion of polyurethane dimethacrylate prepolymers with flexible units. In this particular formulation, it can be seen that although the composite material exhibits excellent deflection-at-break, its flexural strength is poor.

EXAMPLE 3

Accelerator Side:

| Ingredient | Percent |
| --- | --- |
| Urethane dimethacrylate | 27.0 |
| Polyurethane dimethacrylate with Flexible Units | 0.0 |

-continued

| Ingredient | Percent |
| --- | --- |
| polyether dimethacrylate | 7.2 |
| alkyl dimethacrylate | 7.5 |
| Polybutadiene dimethacrylate | 19.2 |
| Glass filler | 33.0 |
| amorphous silica | 5.2 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.
Properties:
Flexural strength (Mpa): 58.5
Deflection-at-break (mm): 1.8
Compressive strength (Mpa): 186
Results:
Example 3 demonstrates yet another polymerized composite material formulation without inclusion of polyurethane dimethacrylate prepolymers with flexible units. In this particular formulation, neither the flexural strength nor deflection-at-break properties are optimal for dental applications.

EXAMPLE 4

Accelerator Side:

| Ingredient | Percent |
| --- | --- |
| Urethane dimethacrylate | 27.0 |
| Polyurethane dimethacrylate with HPB Flexible Units | 19.6 |
| polyether dimethacrylate | 7.2 |
| alkyl dimethacrylate | 7.2 |
| Glass filler | 33.0 |
| amorphous silica | 5.2 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.
Properties:
Flexural strength (Mpa): 66.0
Deflection-at-break (mm): 2.6
Compressive strength (Mpa): 196
Results:
Example 4 demonstrates properties derived by inclusion of the polyurethane dimethacrylate prepolymers wherein the flexible unit is hydrogenated polybutadiene (HPB) of embodiments of the invention. In this formation, with 19.6% by weight of the accelerator side of the flexible polyurethane dimethacrylate (with hydrogenated polybutadiene as the flexible unit), or about 9.8% by weight of the total composite material after combination of the accelerator side and the catalyst side, an excellent flexural strength is achieved in combination with far superior deflection-at-break properties. The mechanical properties of embodiments of the invention in comparison to other commercially available provisional materials are included below in Table 1. Tests were conducted on an Instron Model 1011 Universal Testing Machine. As shown in Table 1, embodiments of the present invention (designated as Tufftemp) have far superior deflection-at-break properties compared to other commercially available provisional materials. Luxatemp is commercially available from DMG of Germany, and Protemp Plus is commercially available from 3M, St. Paul, Minn. As shown in FIG. 1, the toughness of the composite materials produced from embodiments of the invention (Tufftemp), determined by measuring the area under the stress-strain curve obtained from the flexural strength measurements, is substantially greater than and far superior to the aforementioned other commercially available materials. With slight modifications in the amount of polyurethane dimethacrylate prepolymers or the ratio of organic matrix to filler, a deflection-at-break of up to 3.2 mm may be achieved.

TABLE 1

| Group | Luxatemp | Protemp Plus | Tufftemp (self Cure) | Tufftemp (light Cure)[b] |
| --- | --- | --- | --- | --- |
| 10 min. | 13.4 (S.D. 7.0) | 15.2 (S.D. 1.9) | 29.5 (S.D. 3.5) | 54.3 (S.D. 4.9) |
| 24 h[a] | 69.5 (S.D. 6.9) | 72.2 (S.D. 5.6) | 74 (S.D. 3.4) | 76.2 (S.D. 5.3) |
| Toughness[c] | 265 KJ/m$^3$ | 342 KJ/m$^3$ | 431 KJ/m$^3$ | 424 KJ/m$^3$ |

[a]specimens were stored in distilled water at 37° C. for 24 hrs.
[b]specimens were prepared by light curing 40 sec on a PROCURE dental light chamber.
[c]toughness of the material is measured after the specimens were stored for 24 hrs. at 37° C.

EXAMPLE 5

Accelerator Side:

| Ingredient | Percent |
| --- | --- |
| Urethane dimethacrylate | 27.0 |
| Polyurethane dimethacrylate with Polyester Flexible Units | 19.6 |
| polyether dimethacrylate | 7.5 |
| alkyl dimethacrylate | 7.2 |
| Glass filler | 33.0 |
| amorphous silica | 5.2 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.
Properties:
Flexural strength (Mpa): 62.0
deflection (mm): 2.3
Compressive strength (Mpa): 285
Results:
Example 5 demonstrates properties derived by inclusion of the polyurethane dimethacrylate prepolymers wherein the flexible unit is polyester. In this formation, with the flexible polyurethane dimethacrylate accounting for 19.6% by weight of the accelerator side, or about 9.8% by weight of the total composite material, an excellent flexural strength is once again achieved in combination with far superior deflection-at-break properties.

EXAMPLE 6

Accelerator Side:

| Ingredient | Percent |
| --- | --- |
| Urethane dimethacrylate | 40.2 |
| Polyurethane dimethacrylate with HPB Polybutadiene Flexible Units | 10.0 |
| polyether dimethacrylate | 7.5 |
| alkyl dimethacrylate | 2.9 |
| Glass filler | 33.0 |
| amorphous silica | 5.3 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.
Properties:
Flexural strength (Mpa): 84.5
Deflection-at-break (mm): 2.3
Compressive strength (Mpa): 254
Results:
Example 6 demonstrates a polymerized composite material wherein 10% by weight of the accelerator side, or 5% by weight of the total composite, is comprised of polyurethane dimethacrylate prepolymers with hydrogenated polybutadiene flexible units. This material has excellent flexural strength and compressive strength but has a deflection at break lower than Example 4. The material is a good fit for single unit crowns.

EXAMPLE 7

Accelerator Side:

| Ingredient | Percent |
| --- | --- |
| Urethane dimethacrylate | 10.0 |
| Polyurethane dimethacrylate with HPB Polybutadiene Flexible Units | 40.3 |
| polyether dimethacrylate | 7.5 |
| alkyl dimethacrylate | 2.8 |
| Glass filler | 33.2 |
| amorphous silica | 5.3 |
| photoinitiator | 0.14 |
| amine | 0.75 |
| BHT | 0.001 |

Catalyst Side:

| Ingredient | Percent |
| --- | --- |
| Urethane dimethacrylate | 52.3 |
| Polyethylene glycol dimethacrylate | 7.7 |
| Glass filler | 34.0 |
| amorphous silica | 5.4 |
| benzoyl peroxide | 0.73 |
| BHT | 0.035 |

Mixing equal parts of accelerator and catalyst caused the material to cure to a hard resin. The resin mix can also undergo visible light cure polymerization.
Properties:
Flexural strength (Mpa): 48.6
Deflection-at-break (mm): 3.3
Compressive strength (Mpa): 131
Results:
Example 7 demonstrates a polymerized composite material wherein approximately 40% by weight of the accelerator side, or approximately 20% by weight of the total composite, is comprised of polyurethane dimethacrylate prepolymers with hydrogenated polybutadiene flexible units. Although this example has excellent deflection and good flexural properties, it has low compressive strength. This material can be a choice for crown and bridge materials.

EXAMPLE 8

Accelerator Side:

| Ingredient | Percent |
| --- | --- |
| Urethane dimethacrylate | 0.0 |
| Polyurethane dimethacrylate- with HPB Flexible Units | 62.7 |

-continued

| Ingredient | Percent |
| --- | --- |
| polyether dimethacrylate | 0.0 |
| alkyl dimethacrylate | 0.0 |
| Glass filler | 33.7 |
| amorphous silica | 2.7 |
| photoinitiator | 0.14 |
| amine | 0.75 |
| BHT | 0.001 |

Catalyst Side:

| Ingredient | Percent |
| --- | --- |
| Urethane dimethacrylate | 25.9 |
| Polyurethane dimethacrylate-with HPB Flexible Units | 25.9 |
| Polyethylene glycol dimethacrylate | 7.5 |
| Glass filler | 37.1 |
| amorphous silica | 2.8 |
| benzoyl peroxide | 0.73 |
| BHT | 0.030 |

Mixing equal parts of accelerator and catalyst caused the material to cure to a hard resin. The resin mix can also undergo visible light cure polymerization.
Properties:
Flexural strength (Mpa): 35
deflection (mm): 4.4
Compressive strength (Mpa): 103
Results:

Example 8 demonstrates properties derived by inclusion of the polyurethane dimethacrylate prepolymers wherein the flexible unit is hydrogenated polybutadiene. In this formulation, the flexible polyurethane dimethacrylate accounts for 100% of the dimethacrylates on the accelerator side and 43.7% of the dimethacrylates on the catalyst side (about 71.9% by weight of the total dimethacrylates) and 62.7% by weight of the entire accelerator side and 25.9% by weight of the entire catalyst side (about 44.3% by weight of the total composite material). The material exhibits a high degree of deflection at break (4.4 mm), but poor flexural and compressive strengths. Although this material is not suitable for crown and bridge applications, it is suitable as a denture reline material where high toughness as well as a high degree of deflection is required.

Conclusions

Polyurethane dimethacrylate materials with flexible units have greater flexibility than their alkyl dimethacrylate analogues, and provide such flexibility without compromising flexural strength.

What is claimed is:

1. A method of making a radically curable polyurethane dimethacrylate prepolymer comprising:
reacting at least one diisocyanate monomer with a reactive diol in the presence of a catalyst to form a diisocyanate-diol prepolymer;
blending the diisocyanate prepolymer in at least one aprotic methacrylate monomer, and adding 2-hydroxyethyl methacrylate in the presence of a phenolic inhibitor, wherein the reacting includes reacting isophorone diisocyanate and saturated hydroxyl-terminated polybutadiene in the presence of hexamethylene dimethacrylate and dibutyltin dilaurate to form a polyisocyanate prepolymer in 20% hexamethylene dimethacrylate.

2. The method of claim 1, wherein the diisocyanate monomer is further selected from a group consisting of dicyclohexyl methane diisocyanate, tetramethyl xylene diisocyanate, hexamethylene diisocyanate, 4,4 diphenylmethane diisocyanate, tolulene diisocyanate, and combinations thereof.

3. The method of claim 1, wherein the methacrylate monomer is further selected from a group consisting of triethylene glycol dimethacrylate, tetraethylene glycol dimethacrylate, polyethylene glycol dimethacrylate, polyethylene glycol methacrylate monomethyl ether, tetramethylene dimethacrylate, octmethylene dimethacrylate, dodecamethylene dimethacrylate, and combinations thereof.

4. The method of claim 1, wherein the reactive diol is further selected from a group consisting of hydrogenated polybutadiene diol, polyester diol, polyether diol and combinations thereof.

5. The method of claim 1, further comprising reacting the diisocyanate prepolymer with an ethylenically unsaturated monohydroxy compound selected from a group consisting of hydroxyl propyl methacrylate, hydroxyethyl acrylate, hydroxypropyl acrylate, monohydroxy caprolactone methacrylate, hydroxyl butyl methacrylate, monohydroxy polyethylene glycol methacrylate, and combinations thereof.

6. The method of claim 1, further comprising monitoring the reaction with Fourier transform infrared spectroscopy until no free isocyanate groups are detected.

7. The method of claim 1, further comprising adding a phenolic polymerization inhibitor.

8. A radically curable polyurethane dimethacrylate prepolymer for use in dental compositions made according to the method of claim 1.

9. The radically curable polyurethane dimethacrylate prepolymer of claim 8, the polyurethane dimethacrylate prepolymer including at least one reactive diol inserted within a polyurethane dimethacrylate backbone.

10. A dental restoration kit comprising:
a radically curable polyurethane composite, wherein the composite includes a diisocyanate-polybutadiene prepolymer made according to the method of claim 1.

11. The dental restoration kit of claim 10 further comprising a provisional sealant.

* * * * *